United States Patent
Tomita et al.

(10) Patent No.: US 9,937,440 B2
(45) Date of Patent: Apr. 10, 2018

(54) ADSORPTION CARRIER-PACKED COLUMN

(71) Applicant: Toray Industries, Inc., Tokyo (JP)

(72) Inventors: Naotoshi Tomita, Otsu (JP); Kaoru Shimada, Otsu (JP); Yoshiyuki Ueno, Otsu (JP)

(73) Assignee: Toray Industries, Inc. (JP)

( * ) Notice: Subject to any disclaimer, the term of this patent is extended or adjusted under 35 U.S.C. 154(b) by 281 days.

(21) Appl. No.: 14/889,904

(22) PCT Filed: May 30, 2014

(86) PCT No.: PCT/JP2014/064378
§ 371 (c)(1),
(2) Date: Nov. 9, 2015

(87) PCT Pub. No.: WO2014/192908
PCT Pub. Date: Dec. 4, 2014

(65) Prior Publication Data
US 2016/0107100 A1   Apr. 21, 2016

(30) Foreign Application Priority Data

May 31, 2013   (JP) ................................ 2013-115261

(51) Int. Cl.
*B01D 15/22*   (2006.01)
*A61M 1/36*   (2006.01)
(Continued)

(52) U.S. Cl.
CPC ........... *B01D 15/22* (2013.01); *A61M 1/3679* (2013.01); *B01D 29/0022* (2013.01);
(Continued)

(58) Field of Classification Search
CPC .............. A61M 1/3633; A61M 1/3635; A61M 1/3679; B01D 15/22; B01D 29/0022;
(Continued)

(56) References Cited

U.S. PATENT DOCUMENTS 3,701,433 A   10/1972   Krakauer
5,399,264 A * 3/1995   Pulek .................. B01D 29/333
                                                              210/450
(Continued)

FOREIGN PATENT DOCUMENTS

| CN | 101862482 | 10/2010 |
| CN | 202666065 | 1/2013 |
| DE | 33 82 681 | 8/1993 |
| EP | 1 066 843 A1 | 1/2001 |
| EP | 1 553 113 | 7/2005 |
| JP | 2002-172163 | 6/2002 |
| JP | 2003-225304 | 8/2003 |
| JP | 2004-041527 A | 2/2004 |

(Continued)

OTHER PUBLICATIONS

Supplementary European Search Report dated Jan. 2, 2017, of corresponding European Application No. 14804488.6.
(Continued)

*Primary Examiner* — Matthew O Savage
(74) *Attorney, Agent, or Firm* — DLA Piper LLP (US)

(57) ABSTRACT

An adsorption carrier-packed column includes a central pipe, adsorption carrier, plate A, and plate B, wherein an insertion material C is inserted between the adsorption carrier and the plate A; an insertion material D is inserted between the adsorption carrier and the plate B; the ratio of the deformation rate of the insertion material C ($C_1$) to the deformation rate of the adsorption carrier ($E_0$) is $1<C_1/E_0<10$, and the ratio of the deformation rate of the insertion material D ($D_1$) to the deformation rate of the adsorption carrier ($E_0$) is $1<D_1/E_0<10$; and the ratio of the thickness of the insertion material C ($T_C$) to the distance of a gap between the adsorption carrier and the plate A ($L_A$) is $1.1<T_C/L_A<4$, and the ratio of the thickness of the insertion material D ($T_D$) to the distance of a gap between the adsorption carrier and the plate B ($L_B$) is $1.1<T_D/L_B<4$.

11 Claims, 1 Drawing Sheet

(51) Int. Cl.
    *B01D 29/00*    (2006.01)
    *B01J 20/28*    (2006.01)
    *B01J 20/32*    (2006.01)

(52) U.S. Cl.
    CPC ..... *B01J 20/28023* (2013.01); *B01J 20/3208* (2013.01); *B01J 20/3251* (2013.01); *A61M 1/365* (2014.02); *A61M 1/3633* (2013.01); *A61M 2202/0439* (2013.01); *B01D 2201/342* (2013.01); *B01J 2220/58* (2013.01)

(58) Field of Classification Search
    CPC ........... B01D 29/0025; B01D 39/1623; B01D 39/1684; B01D 2201/342; B01D 29/022; B01J 20/280023; B01J 20/3251; B01J 20/3208; B01J 2220/58; B01J 20/28023; B01J 220/582
    USPC ............. 210/441, 450, 497.1; 604/6.03
    See application file for complete search history.

(56) References Cited

U.S. PATENT DOCUMENTS

| | | |
|---|---|---|
| 6,498,007 B1 | 12/2002 | Adachi et al. |
| 2008/0213523 A1 | 9/2008 | Fujimoto et al. |
| 2010/0025335 A1 | 2/2010 | Shimaki |

FOREIGN PATENT DOCUMENTS

| | | |
|---|---|---|
| WO | 02/15964 | 2/2002 |
| WO | 2008/038785 A1 | 4/2008 |

OTHER PUBLICATIONS

The First Office Action dated Aug. 3, 2016, of corresponding Chinese Application No. 201480031050.4, along with an English translation.

\* cited by examiner

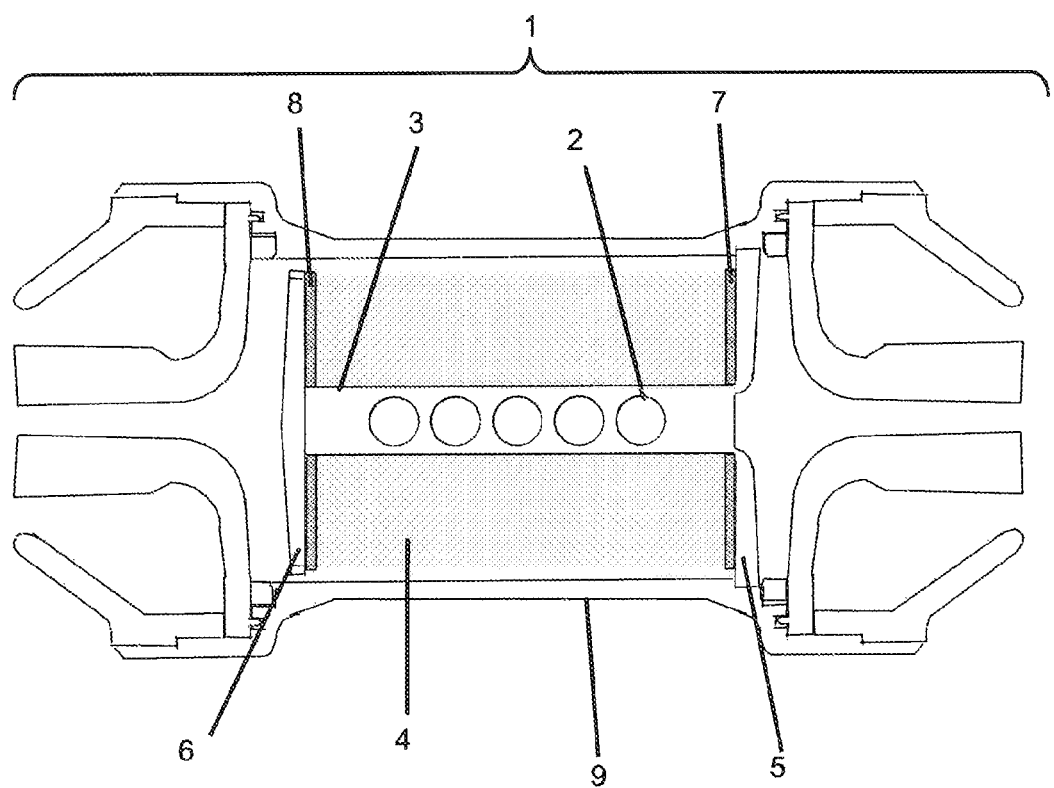

ADSORPTION CARRIER-PACKED COLUMN

TECHNICAL FIELD

This disclosure relates to an adsorption carrier-packed column which reduces bypassing.

BACKGROUND

A variety of columns packed with adsorption carriers have been devised for removal/recovery of unnecessary components from liquids and gases. The structures of the columns can be divided, based on the flow of the medium, into two large groups: the axial flow and the radial flow. The axial flow is used mainly for analysis and fractionation by GC, HPLC, GPC, or the like, and the radial flow is used for body fluid processing columns and the like (JP 2004-41527 A). The radial flow is thought to be especially efficient from the viewpoint of contacting with the carrier, and products in which an adsorption carrier is wound around a central pipe are widely used in the field of extracorporeal circulation (WO 2000/38763).

However, in the conventional radial flow columns described in JP '527 and WO '763, gaps are generated at the inlet and outlet plates arranged above and below the adsorption carrier, and the medium preferentially flows through the gaps, which show no resistance. This causes bypassing, resulting in insufficient exertion of the capacity of the adsorption carrier in some cases. To avoid the bypassing, there are limitations, for example, that each pore on the central pipe cannot be provided in the vicinities of the plates. A countermeasure for the gaps is filling of the gaps with a resin, and urethane resins and epoxy resins are mainly used therefor (CELLSORBA (registered trademark), manufactured by Asahi Kasei Medical Co., Ltd.). Uniform application of urethane resins and epoxy resins requires a technique. Moreover, since they are in the forms of pastes, their operability under clean circumstances is poor and, when the adsorption carrier is wet, use of such resins is restricted so that the resins lack versatility. Furthermore, since a reactive base resin and a curing agent need to be mixed together to produce a resin immediately before the application, there is a possibility that the base resin or the curing agent reacts with the adsorption carrier to cause deterioration of the adsorption carrier, and there are also safety problems such as the irritant nature and harmfulness to operators so that a simpler method has been demanded.

It could therefore be helpful to provide a radial flow column in which an adsorption carrier is packed, wherein the adsorption carrier-packed radial flow column enables maximal exertion of the performance of the adsorption carrier contained therein by reducing bypassing and allowing uniform flow of the flowing liquid.

SUMMARY

We discovered that, when insertion materials having deformation rates of not less than the deformation rate of the adsorption carrier and having thicknesses suitable for the gaps between the absorption carrier and the plates are inserted in the gaps, the gaps between the absorption carrier and the plates can be eliminated so that bypassing can be avoided and the adsorption carrier can be uniformly used. This eliminates the limitation of the position(s) of the pore(s) on the central pipe.

We thus provide (1) to (5) below:
(1) An adsorption carrier-packed column which is a radial flow type adsorption carrier-packed column, comprising:
  a central pipe in which a pore(s) provided for allowing outflow of a supplied liquid is/are formed on a longitudinal side surface(s);
  an adsorption carrier packed in the circumference of the central pipe, for allowing adsorption of a target molecule(s) or a target cell(s) contained in the liquid;
  a plate A communicating with the upstream end of the central pipe such that the inflowing liquid passes through the central pipe, the plate A being arranged such that contacting of the liquid with the adsorption carrier without passing through the central pipe is prevented; and
  a plate B arranged such that the downstream end of the central pipe is sealed and the adsorption carrier is immobilized in the space in the circumference of the central pipe; wherein
  an insertion material C is inserted between the adsorption carrier and the plate A;
  an insertion material D is inserted between the adsorption carrier and the plate B;
  the ratio ($C_1/E_0$) of the deformation rate of the insertion material C ($C_1$) to the deformation rate of the adsorption carrier ($E_0$) is $1<C_1/E_0<10$, and the ratio ($D_1/E_0$) of the deformation rate of the insertion material D ($D_1$) to the deformation rate of the adsorption carrier ($E_0$) is $1<D_1/E_0<10$; and
  the ratio ($T_C/L_A$) of the thickness of the insertion material C ($T_C$) to the distance of a gap between the adsorption carrier and the plate A ($L_A$) is $1.1<T_C/L_A<4$, and the ratio ($T_D/L_B$) of the thickness of the insertion material D ($T_D$) to the distance of a gap between the adsorption carrier and the plate B ($L_B$) is $1.1<T_D/L_B<4$.
(2) The adsorption carrier-packed column according to (1), wherein the ratio ($T_C/L_A$) of the thickness of the insertion material C ($T_C$) to the distance of the gap between the adsorption carrier and the plate A ($L_A$) is $3<T_C/L_A<4$, and the ratio ($T_D/L_B$) of the thickness of the insertion material D ($T_D$) to the distance of the gap between the adsorption carrier and the plate B ($L_B$) is $3<T_D/L_B<4$.
(3) The adsorption carrier-packed column according to (1) or (2), wherein each of the insertion materials C and D is independently an insertion material composed of a rubber, gel, sponge, or non-woven fabric, or an insertion material containing any of these as a raw material(s).
(4) The adsorption carrier-packed column according to any one of (1) to (3), for blood component processing.
(5) The adsorption carrier-packed column according to any one of (1) to (4), for removal of IL-6.

An adsorption carrier-packed column that enables reduction of bypassing and improvement of the performance of the adsorption carrier can be provided.

BRIEF DESCRIPTION OF THE DRAWING

FIG. 1 is a schematic diagram showing the structure of our adsorption carrier-packed column.

DESCRIPTION OF SYMBOLS 1 adsorption carrier-packed column
2 pore
3 central pipe 4 adsorption carrier
5 plate A
6 plate B
7 insertion material C
8 insertion material D
9 container

DETAILED DESCRIPTION

The adsorption carrier-packed column is characterized in that it is a radial flow type adsorption carrier-packed column comprising:
- a central pipe in which a pore(s) provided for allowing outflow of a supplied liquid is/are formed on a longitudinal side surface(s);
- an adsorption carrier packed in the circumference of the central pipe, for allowing adsorption of a target molecule(s) or a target cell(s) contained in the liquid;
- a plate A communicating with the upstream end of the central pipe such that the inflowing liquid passes through the central pipe, the plate A being arranged such that contacting of the liquid with the adsorption carrier without passing through the central pipe is prevented; and
- a plate B arranged such that the downstream end of the central pipe is sealed and the adsorption carrier is immobilized in the space in the circumference of the central pipe; wherein
- an insertion material C is inserted between the adsorption carrier and the plate A;
- an insertion material D is inserted between the adsorption carrier and the plate B;
- the ratio ($C_1/E_0$) of the deformation rate of the insertion material C ($C_1$) to the deformation rate of the adsorption carrier ($E_0$) is $1<C_1/E_0<10$, and the ratio ($D_1/E_0$) of the deformation rate of the insertion material D ($D_1$) to the deformation rate of the adsorption carrier ($E_0$) is $1<D_1/E_0<10$; and
- the ratio ($T_C/L_A$) of the thickness of the insertion material C ($T_C$) to the distance of a gap between the adsorption carrier and the plate A ($L_A$) is $1.1<T_C/L_A<4$, and the ratio ($T_D/L_B$) of the thickness of the insertion material D ($T_D$) to the distance of a gap between the adsorption carrier and the plate B ($L_B$) is $1.1<T_D/L_B<4$.

Preferred examples are described below in detail with reference to a drawing, but this disclosure is not limited to these examples. The ratios in the drawing are not necessarily the same as those described below.

The adsorption carrier-packed column 1 shown in FIG. 1 has a central pipe 3, adsorption carrier 4, plate 5, plate 6, insertion material 7, and insertion material 8. These structures are arranged in a container 9.

The central pipe 3 is a pipe having a cylindrical shape wherein a pore(s) 2 provided to allow outflow of a supplied liquid is/are formed on a longitudinal side surface(s). In this example, in the central pipe 3, five pores 2 are formed on one side of the cylindrical shape, and a pore(s) 2, which are not shown, are formed on another side. However, the number of the pores is not limited and may be set appropriately. The material of the central pipe may be any material as long as the material is inert to the solvent used and the substance to be adsorbed/removed.

The adsorption carrier 4 is the carrier packed in the circumference of the central pipe 3. The liquid supplied to the adsorption carrier-packed column 1 passes through the central pipe 3, and flows out from the pores 2 into the adsorption carrier 4, where the adsorption carrier 4 adsorbs a target molecule(s) or target cell(s) contained in the liquid. The adsorption carrier 4 may be packed as a cylindrical carrier in the circumference of the central pipe 3 by winding of a sheet-shaped non-woven fabric around the central pipe 3. However, the shape of the adsorption carrier and the method of packing of the adsorption carrier are not limited, and the adsorption carrier may be any adsorption carrier as long as it can be arranged in the container 9. The material of the adsorption carrier is appropriately selected depending on the type of the target molecule or the target cell to be adsorbed.

The plate 5 is a plate-shaped member to prevent the liquid from contacting with the adsorption carrier 4 without passing through the central pipe 3. The plate 5 is arranged such that the plate 5 communicates with the upstream end of the central pipe 3 to make the liquid flowing into the adsorption carrier-packed column 1 pass through the central pipe 3. The plate 6 is a plate-shaped member to prevent the liquid that has flowed into the adsorption carrier-packed column 1 from flowing without passing through the pores 2. The plate 6 is arranged such that the downstream end of the central pipe 3 is sealed and the adsorption carrier 4 is immobilized in the space in the circumference of the central pipe 3. The shapes of the plate 5 and the plate 6 are not limited, and may be any shapes as long as the plates can be arranged in the container 9. The materials of the plate 5 and the plate 6 are not limited, and may be any materials as long as the materials are inert to the solvent used and the substance to be adsorbed/removed.

The insertion material is inserted between the adsorption carrier and the plates to fill the gaps between the adsorption carrier and the plates. The insertion material 7 may be inserted between the adsorption carrier 4 and the plate 5 by sandwiching the insertion material 7 between the adsorption carrier 4 and the plate 5. The insertion material 8 may be inserted between the adsorption carrier 4 and the plate 6 by sandwiching the insertion material 8 between the adsorption carrier 4 and the plate 6.

The deformation rate is a value indicating the extent of deformation that occurs when a certain pressure is applied to a member such as an adsorption carrier or an insertion material. The higher the deformation rate, the more likely deformation occurs. The deformation rate is defined by Equation (1) below:

$$\text{Deformation rate} = (\text{natural length} - \text{length after application of load})/\text{pressure applied} \qquad (1).$$

For example, when a load of 10 g (pressure, 10 g/cm$^2$) is uniformly applied to the bottom surface of an insertion material having a bottom surface area of 1 cm$^2$ and a natural length of 1 cm, and the length becomes 0.8 cm thereafter, the deformation rate is as follows:

$$\text{Deformation rate} = (1-0.8)/(10/1) = 0.02 \text{ cm}^3/\text{g}.$$

When a load of 20 g (pressure, 2 g/cm$^2$) is uniformly applied to the bottom surface of an insertion material having a bottom surface area of 10 cm$^2$ and a natural length of 5 cm, and the length becomes 4.5 cm thereafter, the deformation rate is as follows:

$$\text{Deformation rate} = (5-4.5)/(20/10) = 0.25 \text{ cm}^3/\text{g}.$$

The deformation rate of each insertion material is preferably not less than the deformation rate of the adsorption carrier since, when the deformation rate of the insertion material is too low, the adsorption carrier is pushed back and deformed because of low flexibility of the insertion material, resulting in generation of an irregular flow. On the other hand, when the deformation rate is too high, deformation of the insertion material occurs even with a weak force, causing insufficient filling of the gap between the absorption material and the plate, and the insertion material cannot tolerate the force caused by the flow of the medium supplied so that bypassing cannot be prevented. Thus, the deformation rate of the insertion material is preferably not more than 10%. The deformation rate may be different between the insertion materials in the upstream end side and the downstream end side of the central pipe.

When the thickness in the longitudinal direction of each insertion material is too small, the gap cannot be sufficiently filled, and bypassing occurs. The thickness is therefore preferably not less than the distance of the gap between the adsorption carrier and the plate. When the thickness is too large, deformation of the adsorption carrier occurs, and a gap is generated between the insertion material and the adsorption carrier, resulting in occurrence of bypassing. Judging from the Examples described below, the longitudinal thickness of the insertion material is preferably not more than four times the distance of the gap between the adsorption carrier and the plate. The thickness may be different between the insertion materials in the upstream end side and the downstream end side of the central pipe.

The deformation rate of the adsorption carrier is hereinafter defined as $E_0$. The deformation rate of the insertion material C sandwiched between the adsorption carrier and the plate A is defined as $C_1$; the longitudinal thickness of the insertion material C is defined as $T_C$; and the distance of the gap between the adsorption carrier and the plate A in the absence of the insertion material C sandwiched therebetween is defined as $L_A$. The deformation rate of the insertion material D sandwiched between the adsorption carrier and the plate B is defined as $D_1$; the longitudinal thickness of the insertion material D is defined as $T_D$; and the distance of the gap between the adsorption carrier and the plate B in the absence of the insertion material D sandwiched therebetween is defined as $L_B$.

The material of each insertion material is not limited as long as the material is inert to the solvent used and the substance to be adsorbed/removed, and examples of the material include rubbers such as natural rubbers, nitrile rubbers, isoprene rubbers, urethane rubbers, ethylene-propylene rubbers, chlorosulfonated polyethylenes, epichlorohydrin rubbers, chloroprene rubbers, silicone rubbers, styrene-butadiene rubbers, butadiene rubbers, fluorocarbon rubbers, and polyisobutylenes. Other than rubbers, examples of the material include sponges, non-woven fabrics, and gels, as long as these satisfy the required rate of change. When the column is used for the purpose of adsorption, the same material as that of the adsorption carrier is preferably used for the insertion material, from the viewpoint of further increasing the performance. The material may be different between the insertion materials in the upstream end side and the downstream end side of the central pipe.

The insertion material is preferably entirely filled between the adsorption carrier and the plate, and the shape of the insertion material may be any shape. However, for the insertion material to be entirely filled between the adsorption carrier and the plate, the insertion material preferably has a doughnut-like shape whose central hole is designed to have a size with which the insertion material tightly fits the central pipe portion. For an increased adhesion between the plate and the adsorption carrier, the surface of the insertion material contacting with the adsorption carrier is preferably irregular.

In terms of the shape of the container of the column packed with the adsorption carrier, the container may be a container having an inlet and an outlet for blood, and having a size that allows packing of the adsorption carrier wound in a cylindrical shape around the central pipe as an axis; and may be a container wherein blood flows from the outer circumference to the inside of the cylinder and then flows out of the container, or a container wherein blood flows from the inside to the outside of the cylinder and then flows out of the container. Although a cylindrical container is used in this example, the container is not limited thereto, and examples of the container include cylindrical containers, triangular prism-shaped containers, quadrangular prism-shaped containers, hexagonal prism-shaped containers, and octagonal prism-shaped containers.

The extent of the reduction of bypassing in the column can be investigated by allowing a substance having affinity to the packed adsorption carrier, or a substance that adsorbs to the adsorption carrier, to pass through the column. For example, when the adsorption carrier is known to adsorb a dye, an aqueous solution of the dye may be allowed to pass through the column, and the extent to which the adsorption carrier is stained may be investigated to qualitatively know the extent of bypassing. In cases of an adsorption carrier that adsorbs a protein such as a cytokine in a blood component removal column or the like, reduction of the bypassing and improvement of the performance can be quantitatively known by allowing a solution of the cytokine of interest to pass through the column and detecting the change in the concentration by ELISA or the like.

The target molecule means a molecule which can be adsorbed to the adsorption carrier, contained in the liquid which flows into the column. The target cell means a cell which can be adsorbed to the adsorption carrier, contained in the liquid which flows into the column. The blood component means a component constituting blood, and examples of the blood component include blood cell components such as erythrocytes, leukocytes, and platelets; and humoral factors such as cytokines Among these, for the purpose of treatment of inflammatory diseases, leukocytes and cytokines are preferably removed by adsorption.

A cytokine means a protein secreted from cells that transmit information to specific cells, and examples of cytokines include interleukins, tumor necrosis factor-α, transforming growth factor β, interferon-γ (hereinafter referred to as INF-γ), angiogenic growth factors, and immunosuppressive acidic proteins.

An interleukin means a cytokine which is secreted from leukocytes and functions for immunoregulation, and examples of interleukins include interleukin-1, interleukin-6, interleukin-8 (hereinafter referred to as IL-8), interleukin-10, and interleukin-17 (hereinafter referred to as IL-17).

EXAMPLES

Preparation of PP Non-Woven Fabric

A sea-island composite fiber with 36 islands in which each island further has a core-sheath composite structure was obtained using the following components at a spinning speed of 800 m/minute and a draw ratio of 3.

Core component of island: Polypropylene
Sheath component of island: Polystyrene, 90 wt %
   Polypropylene, 10 wt %
Sea component: Copolymerized polyester containing ethylene terephthalate units as major repeating units, and also containing 3 wt % sodium 5-sulfoisophthalate as a copolymerizing component.

Mixing ratio (weight ratio): Core:sheath:sea=45:40:15

A non-woven fabric composed of the resulting fiber at 85 wt % and a polypropylene fiber with a diameter of 20 µm at 15 wt % was prepared, and a sheet-shaped polypropylene net (thickness, 0.5 mm; single yarn diameter, 0.3 mm; opening, 2 mm×2 mm) was sandwiched between two sheets of the resulting non-woven fabric, followed by needle punching, to obtain a non-woven fabric with a three-layer structure (hereinafter referred to as PP non-woven fabric).

Preparation of PSt-PP Non-Woven Fabric

The PP non-woven fabric was treated at 95° C. with 3 wt % aqueous sodium hydroxide solution to dissolve the sea component, thereby preparing a non-woven fabric (PSt+PP non-woven fabric, hereinafter referred to as Non-woven fabric A) in which the diameter of the core-sheath fiber is 5 µm and the bulk density is 0.02 g/cm³.

Preparation of Chloroacetamidomethylated Non-Woven Fabric

An N-methylol-α-chloroacetamide (hereinafter referred to as NMCA) modification reaction liquid was prepared by mixing, stirring, and dissolving 46 wt % nitrobenzene, 46 wt % sulfuric acid, 1 wt % paraformaldehyde, and 7 wt % NMCA together at not more than 10° C. The temperature of the resulting NMCA modification liquid was adjusted to 5° C., and the NMCA modification liquid was added to Non-woven fabric A at a solid-liquid ratio of about 40 mL of the liquid per 1 g of the fabric. The reaction liquid was then allowed to react in a water bath for 2 hours while the temperature was kept at 5° C. Thereafter, the non-woven fabric was removed from the reaction liquid, and washed by immersion in nitrobenzene in the same amount as the NMCA reaction liquid. The non-woven fabric was then removed therefrom, and washed by immersion in methanol to obtain a chloroacetamidomethylated non-woven fabric (hereinafter referred to as Non-woven fabric B).

Preparation of Tetraethylenepentamine-Modified Non-Woven Fabric

Tetraethylenepentamine (hereinafter referred to as TEPA) and triethylamine were dissolved in 500 mL of dimethylsulfoxide (hereinafter referred to as DMSO) such that the TEPA concentration was 20 mM and the triethylamine concentration was 473 mM. In the resulting solution, 10 g of Non-woven fabric B was immersed to allow the reaction to proceed at 40° C. for 3 hours. The non-woven fabric after the reaction was washed with DMSO and methanol, and then with water, to obtain a TEPA-modified non-woven fabric (hereinafter referred to as Non-woven fabric C). The deformation rate of Non-woven fabric C ($E_0$) was 0.021 cm³/g. Non-woven fabric C adsorbs methyl orange and IL-6.

Example 1

A sheet of Non-woven fabric C with a size of 4.5 cm×47 cm was wound seven times around a central pipe and, when the resultant was sandwiched between upper and lower plates, each of two doughnut-shaped sheets of Non-woven fabric C (deformation rate, $C_1=D_1=0.021$ cm³/g; thickness, $T_C=T_D=2.0$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 0.75 g/500 mL aqueous methyl orange solution was allowed to flow at a flow rate of 30 mL/min. for 3 minutes. Subsequently, water was allowed to flow for washing, and the column was then disassembled for observation of staining of the adsorption carrier. When an area unstained with methyl orange (white spot) was found on the adsorption carrier, the adsorption carrier was judged as "spotted," while when the entire area was stained, the adsorption carrier was judged as "unspotted." As a result, the adsorption carrier was judged as "unspotted" as shown in Table 1.

Example 2

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.023$ cm³/g; thickness, $T_C=T_D=1.8$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 500 pg/500 mL aqueous methyl orange solution was allowed to flow at a flow rate of 30 mL/min. for 3 minutes. Subsequently, water was allowed to flow for washing, and the column was then disassembled for observation of staining of the adsorption carrier. As a result, the adsorption carrier was judged as "unspotted" as shown in Table 1.

Example 3

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.2$ cm³/g; thickness, $T_C=T_D=1.8$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 500 pg/500 mL aqueous methyl orange solution was allowed to flow at a flow rate of 30 mL/min. for 3 minutes. Subsequently, water was allowed to flow for washing, and the column was then disassembled for observation of staining of the adsorption carrier. As a result, the adsorption carrier was judged as "unspotted" as shown in Table 1.

Example 4

A sheet of Non-woven fabric C with a size of 4.5 cm×47 cm was wound seven times around a central pipe and, when the resultant was sandwiched between upper and lower plates, each of two doughnut-shaped sheets of Non-woven fabric C (deformation rate, $C_1=D_1=0.021$ cm³/g; thickness, $T_C=T_D=1.5$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 500 pg/500 mL aqueous methyl orange solution was allowed to flow at a flow rate of 30 mL/min. for 3 minutes. Subsequently, water was allowed to flow for washing, and the column was then disassembled for observation of staining of the adsorption carrier. As a result, the adsorption carrier was judged as "unspotted" as shown in Table 1.

Example 5

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.023$ cm$^3$/g; thickness, $T_C=T_D=0.5$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 500 pg/500 mL aqueous methyl orange solution was allowed to flow at a flow rate of 30 mL/min. for 3 minutes. Subsequently, water was allowed to flow for washing, and the column was then disassembled for observation of staining of the adsorption carrier. As a result, the adsorption carrier was judged as "unspotted" as shown in Table 1.

Comparative Example 1

A sheet of Non-woven fabric C with a size of 4.5 cm×47 cm was wound seven times around a central pipe, and the resultant was sandwiched between upper and lower plates, followed by packing the resulting construct in a radial flow column case having an inlet and an outlet for a medium. The distance of the gap between the Non-woven fabric C and each plate was 0.5 mm. Through this column, 0.75 g/500 mL aqueous methyl orange solution was allowed to flow at a flow rate of 30 mL/min. for 3 minutes. Subsequently, water was allowed to flow for washing, and the column was then disassembled for observation of staining of the adsorption carrier. As a result, the adsorption carrier was judged as "spotted" as shown in Table 1.

Comparative Example 2

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.018$ cm$^3$/g; thickness, $T_C=T_D=1.7$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 0.75 g/500 mL aqueous methyl orange solution was allowed to flow at a flow rate of 30 mL/min. for 3 minutes. Subsequently, water was allowed to flow for washing, and the column was then disassembled for observation of staining of the adsorption carrier. As a result, the adsorption carrier was judged as "spotted" as shown in Table 1.

Comparative Example 3

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.25$ cm$^3$/g; thickness, $T_C=T_D=1.8$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 0.75 g/500 mL aqueous methyl orange solution was allowed to flow at a flow rate of 30 mL/min. for 3 minutes. Subsequently, water was allowed to flow for washing, and the column was then disassembled for observation of staining of the adsorption carrier. As a result, the adsorption carrier was judged as "spotted" as shown in Table 1.

Comparative Example 4

A sheet of Non-woven fabric C with a size of 4.5 cm×47 cm was wound seven times around a central pipe and, when the resultant was sandwiched between upper and lower plates, each of two doughnut-shaped sheets of Non-woven fabric C (deformation rate, $C_1=D_1=0.021$ cm$^3$/g; thickness, $T_C=T_D=2.3$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 0.75 g/500 mL aqueous methyl orange solution was allowed to flow at a flow rate of 30 mL/min. for 3 minutes. Subsequently, water was allowed to flow for washing, and the column was then disassembled for observation of staining of the adsorption carrier. As a result, the adsorption carrier was judged as "spotted" as shown in Table 1.

Comparative Example 5

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.023$ cm$^3$/g; thickness, $T_C=T_D=0.4$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 0.75 g/500 mL aqueous methyl orange solution was allowed to flow at a flow rate of 30 mL/min. for 3 minutes. Subsequently, water was allowed to flow for washing, and the column was then disassembled for observation of staining of the adsorption carrier. As a result, the adsorption carrier was judged as "spotted" as shown in Table 1.

Comparative Example 6

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.2$ cm$^3$/g; thickness, $T_C T_D=0.4$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 0.75 g/500 mL aqueous methyl orange solution was allowed to flow at a flow rate of 30 mL/min. for 3 minutes. Subsequently, water was allowed to flow for washing, and the column was then disassembled for observation of staining of the adsorption carrier. As a result, the adsorption carrier was judged as "spotted" as shown in Table 1.

Example 6

A sheet of Non-woven fabric C with a size of 4.5 cm×47 cm was wound seven times around a central pipe and, when the resultant was sandwiched between upper and lower plates, each of two doughnut-shaped sheets of Non-woven fabric C (deformation rate, $C_1=D_1=0.021$ cm$^3$/g; thickness, $T_C=T_D=2.0$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 300 mL of 500 pg/mL interleukin 6 (IL-6) FBS (fetal bovine serum) was allowed to circulate at a flow rate of 30 mL/min. for 60 minutes. As a result of the circulation, the IL-6 concentrations at Minute 0 and Minute 60 were 498 pg/mL and 320 pg/mL, respectively. Thus, the IL-6 adsorption rate was calculated as 35.7% according to Equation (2) shown below (Table 1):

IL-6 adsorption rate (%)=[{(IL-6 concentration at Minute 0)−(IL-6 concentration at Minute 60)}/ IL-6 concentration at Minute 0]×100    (2).

Example 7

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.023$ cm$^3$/g; thickness, $T_C=T_D=1.8$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 300 mL of 500 pg/mL interleukin 6 (IL-6) FBS (fetal bovine serum) was allowed to circulate at a flow rate of 30 mL/min. for 60 minutes. As a result of the circulation, the IL-6 concentrations at Minute 0 and Minute 60 were 495 pg/mL and 395 pg/mL, respectively. Thus, the IL-6 adsorption rate was calculated as 20.7% according to Equation (2) (Table 1).

Example 8

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.2$ cm$^3$/g; thickness, $T_C=T_D=1.8$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 300 mL of 500 pg/mL interleukin 6 (IL-6) FBS (fetal bovine serum) was allowed to circulate at a flow rate of 30 mL/min. for 60 minutes. As a result of the circulation, the IL-6 concentrations at Minute 0 and Minute 60 were 498 pg/mL and 405 pg/mL, respectively. Thus, the IL-6 adsorption rate was calculated as 18.7% according to Equation (2) (Table 1).

Example 9

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.021$ cm$^3$/g; thickness, $T_C=T_D=1.5$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 300 mL of 500 pg/mL interleukin 6 (IL-6) FBS (fetal bovine serum) was allowed to circulate at a flow rate of 30 mL/min. for 60 minutes. As a result of the circulation, the IL-6 concentrations at Minute 0 and Minute 60 were 500 pg/mL and 348 pg/mL, respectively. Thus, the IL-6 adsorption rate was calculated as 30.4% according to Equation (2) (Table 1).

Example 10

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.023$ cm$^3$/g; thickness, $T_C=T_D=0.5$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 300 mL of 500 pg/mL interleukin 6 (IL-6) FBS (fetal bovine serum) was allowed to circulate at a flow rate of 30 mL/min. for 60 minutes. As a result of the circulation, the IL-6 concentrations at Minute 0 and Minute 60 were 498 pg/mL and 406 pg/mL, respectively. Thus, the IL-6 adsorption rate was calculated as 18.5% according to Equation (2) (Table 1).

Comparative Example 7

A sheet of Non-woven fabric C with a size of 4.5 cm×47 cm was wound seven times around a central pipe, and the resultant was sandwiched between upper and lower plates, followed by packing the resulting construct in a radial flow column case having an inlet and an outlet for a medium. The distance of the gap between the Non-woven fabric C and each plate was 0.5 mm. Through this column, 300 mL of 500 pg/mL interleukin 6 (IL-6) FBS (fetal bovine serum) was allowed to circulate at a flow rate of 30 mL/min. for 60 minutes. As a result of the circulation, the IL-6 concentrations at Minute 0 and Minute 60 were 498 pg/mL and 442 pg/mL, respectively. Thus, the IL-6 adsorption rate was calculated as 9.8% according to Equation (2) (Table 1).

Comparative Example 8

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.018$ cm$^3$/g; thickness, $T_C=T_D=1.7$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 300 mL of 500 pg/mL interleukin 6 (IL-6) FBS (fetal bovine serum) was allowed to circulate at a flow rate of 30 mL/min. for 60 minutes. As a result of the circulation, the IL-6 concentrations at Minute 0 and Minute 60 were 498 pg/mL and 442 pg/mL, respectively. Thus, the IL-6 adsorption rate was calculated as 11.2% according to Equation (2) (Table 1).

Comparative Example 9

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.25$ cm$^3$/g; thickness, $T_C=T_D=1.8$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 300 mL of 500 pg/mL interleukin 6 (IL-6) FBS (fetal bovine serum) was allowed to circulate at a flow rate of 30 mL/min. for 60 minutes. As a result of the circulation, the IL-6 concentrations at Minute 0 and Minute 60 were 500 pg/mL and 439 pg/mL, respectively. Thus, the IL-6 adsorption rate was calculated as 11.8% according to Equation (2) (Table 1).

Comparative Example 10

A sheet of Non-woven fabric C with a size of 4.5 cm×47 cm was wound seven times around a central pipe and, when the resultant was sandwiched between upper and lower plates, each of two doughnut-shaped sheets of Non-woven fabric C (deformation rate, $C_1=D_1=0.021$ cm$^3$/g; thickness, $T_C=T_D=2.3$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 300 mL of 500 pg/mL interleukin 6 (IL-6) FBS (fetal bovine serum) was allowed to circulate at a flow rate of 30 mL/min. for 60 minutes. As a result of the circulation, the IL-6 concentrations at Minute 0 and Minute 60 were 500 pg/mL and 437 pg/mL, respectively. Thus, the IL-6 adsorption rate was calculated as 12.2% according to Equation (2) (Table 1).

Comparative Example 11

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.023$ cm$^3$/g; thickness, $T_C=T_D=0.4$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 300 mL of 500 pg/mL interleukin 6 (IL-6) FBS (fetal bovine serum) was allowed to circulate at a flow rate of 30 mL/min. for 60 minutes. As a result of the circulation, the IL-6 concentrations at Minute 0 and Minute 60 were 500 pg/mL and 458 pg/mL, respectively. Thus, the IL-6 adsorption rate was calculated as 8.4% according to Equation (2) (Table 1).

Comparative Example 12

A sheet of Non-woven fabric C with a size of 4.5 cm×47 cm was wound seven times around a central pipe and, when the resultant was sandwiched between upper and lower plates, each of two doughnut-shaped sheets of silicone (deformation rate, $C_1=D_1=0.2$ cm$^3$/g; thickness, $T_C=T_D=0.4$ mm) as insertion materials was sandwiched between the Non-woven fabric C present at each end of the central pipe and each plate (distance of the gap, $L_A=L_B=0.5$ mm), followed by packing the resulting construct in a radial flow column case having an inlet and an outlet for a medium. Through this column, 300 mL of 500 pg/mL interleukin 6 (IL-6) FBS (fetal bovine serum) was allowed to circulate at a flow rate of 30 mL/min. for 60 minutes. As a result of the circulation, the IL-6 concentrations at Minute 0 and Minute 60 were 500 pg/mL and 453 pg/mL, respectively. Thus, the IL-6 adsorption rate was calculated as 9.4% according to Equation (2) (Table 1).

TABLE 1

| Example | $E_0$ (cm$^3$/g) | $C_1$, $D_1$ (cm$^3$/g) | $C_1/E_0$, $D_1/E_0$ | $L_A$, $L_B$ (mm) | $T_C$, $T_D$ (mm) | $T_C/L_A$, $T_D/L_B$ | Methyl orange staining | IL-6 adsorption rate (%) |
|---|---|---|---|---|---|---|---|---|
| Example 1 | 0.021 | 0.021 | 1.0 | 0.5 | 2.0 | 4.0 | Unspotted | |
| Example 6 | | | | | | | | 35.7 |
| Example 2 | | | | | | | Unspotted | |
| Example 7 | 0.021 | 0.023 | 1.1 | 0.5 | 1.8 | 3.6 | | 20.7 |
| Example 3 | | | | | | | Unspotted | |
| Example 8 | 0.021 | 0.2 | 9.5 | 0.5 | 1.8 | 3.6 | | 18.7 |
| Example 4 | | | | | | | Unspotted | |
| Example 9 | 0.021 | 0.021 | 1.0 | 0.5 | 1.5 | 3.0 | | 30.4 |
| Example 5 | | | | | | | Unspotted | |
| Example 10 | 0.021 | 0.023 | 1.1 | 0.5 | 0.5 | 1.0 | | 18.5 |
| Comparative Example 1 | | | | | | | Spotted | |
| Comparative Example 7 | 0.021 | | | 0.5 | | | | 9.8 |
| Comparative Example 2 | | | | | | | Spotted | |
| Comparative Example 8 | 0.021 | 0.018 | 0.9 | 0.5 | 1.7 | 3.4 | | 11.2 |

TABLE 1-continued

| Example | $E_0$ (cm³/g) | $C_1, D_1$ (cm³/g) | $C_1/E_0$, $D_1/E_0$ | $L_A, L_B$ (mm) | $T_C, T_D$ (mm) | $T_C/L_A$, $T_D/L_B$ | Methyl orange staining | IL-6 adsorption rate (%) |
|---|---|---|---|---|---|---|---|---|
| Comparative Example 3 | | | | | | | Spotted | |
| Comparative Example 9 | 0.021 | 0.25 | 11.9 | 0.5 | 1.8 | 3.6 | | 11.8 |
| Comparative Example 4 | | | | | | | Spotted | |
| Comparative Example 10 | 0.021 | 0.021 | 1.0 | 0.5 | 2.3 | 4.6 | | 12.1 |
| Comparative Example 5 | | | | | | | Spotted | |
| Comparative Example 11 | 0.021 | 0.023 | 1.1 | 0.5 | 0.4 | 0.8 | | 8.4 |
| Comparative Example 6 | | | | | | | Spotted | |
| Comparative Example 12 | 0.021 | 0.2 | 9.5 | 0.5 | 0.4 | 0.8 | | 9.4 |

$E_0$: deformation rate of adsorption carrier;
$C_1, D_1$: deformation rate of insertion material;
$L_A, L_B$: distance of gap between adsorption carrier and plate;
$T_C, T_D$: thickness of insertion material From the results in Table 1, it is clear that the adsorption carrier-packed column reduces bypassing and shows remarkable blood component adsorption capacity

INDUSTRIAL APPLICABILITY

We provide an adsorption carrier-packed column packed with an adsorption carrier for removal/recovery of an unnecessary component from a liquid or a gas, which adsorption carrier-packed column is capable of reducing bypassing, and improving the performance of the adsorption carrier.

The invention claimed is:

1. A radial flow adsorption carrier-packed column comprising:
   a central pipe in which at least one pore is provided to allow outflow of a supplied liquid, wherein the at least one pore is formed on at least one longitudinal side surface of the central pipe;
   an adsorption carrier packed on a circumference of said central pipe to allow adsorption of at least one target molecule or at least one target cell contained in said liquid;
   a plate A communicating with an upstream end of said central pipe such that said inflowing liquid passes through said central pipe, said plate A being arranged such that contacting of said liquid with said adsorption carrier without passing through said central pipe is prevented; and
   a plate B arranged such that a downstream end of said central pipe is sealed and said adsorption carrier is immobilized in a space in a circumference of said central pipe;
   wherein
   an insertion material C is inserted between said adsorption carrier and said plate A;
   an insertion material D is inserted between said adsorption carrier and said plate B;
   a ratio ($C_1/E_0$) of a deformation rate $C_1$ of said insertion material C to a deformation rate $E_0$ of said adsorption carrier is $1 \leq C_1/E_0 \leq 10$, and a ratio ($D_1/E_0$) of a deformation rate $D_1$ of said insertion material D to a deformation rate $E_0$ of said adsorption carrier is $1 \leq D_1/E_0 \leq 10$; and
   a ratio ($T_C/L_A$) of a thickness $T_C$ of said insertion material C to a distance $L_A$ of a gap between said adsorption carrier and said plate A is $1.1 \leq T_C/L_A \leq 4$, and a ratio ($T_D/L_B$) of a thickness $T_D$ of said insertion material D to a distance $L_B$ of a gap between said adsorption carrier and said plate B is $1.1 \leq T_D/L_B \leq 4$.

2. The adsorption carrier-packed column according to claim 1, wherein the ratio ($T_C/L_A$) of the thickness $T_C$ of said insertion material C to the distance $L_A$ of the gap between said adsorption carrier and said plate A is $3 \leq T_C/L_A \leq 4$, and the ratio ($T_D/L_B$) of the thickness $T_D$ of said insertion material D to the distance $L_B$ of the gap between said adsorption carrier and said plate B is $3 \leq T_D/L_B \leq 4$.

3. The adsorption carrier-packed column according to claim 2, wherein said insertion materials C and D are independently selected from the group consisting of rubber, gel, sponge, non-woven fabric and combinations thereof.

4. The adsorption carrier-packed column according to claim 2, wherein said adsorption carrier includes means for processing blood.

5. The adsorption carrier-packed column according to claim 2, wherein said adsorption carrier includes means for removing IL-6 from said liquid.

6. The adsorption carrier-packed column according to claim 1, wherein said insertion materials C and D are independently selected from the group consisting of rubber, gel, sponge, non-woven fabric and combinations thereof.

7. The adsorption carrier-packed column according to claim 6, wherein said adsorption carrier includes means for processing blood.

8. The adsorption carrier-packed column according to claim 6, wherein said adsorption carrier includes means for removing IL-6 from said liquid.

9. The adsorption carrier-packed column according to claim 1, wherein said adsorption carrier includes means for processing blood.

10. The adsorption carrier-packed column according to claim 9, wherein said adsorption carrier includes means for removing IL-6 from said liquid.

11. The adsorption carrier-packed column according to claim 1, wherein said adsorption carrier includes means for removing IL-6 from said liquid.

* * * * *